(12) United States Patent
Chang

(10) Patent No.: US 9,775,582 B2
(45) Date of Patent: Oct. 3, 2017

(54) MEDICAL IMAGE PHOTOGRAPHING APPARATUS AND METHOD OF PROCESSING MEDICAL IMAGE

(71) Applicant: SAMSUNG ELECTRONICS CO., LTD., Suwon-si (KR)

(72) Inventor: Sung-ho Chang, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/729,566

(22) Filed: Jun. 3, 2015

(65) Prior Publication Data

US 2016/0015350 A1 Jan. 21, 2016

(30) Foreign Application Priority Data

Jul. 18, 2014 (KR) ........................ 10-2014-0091320

(51) Int. Cl.
*G06T 11/00* (2006.01)
*A61B 6/00* (2006.01)
*A61B 6/03* (2006.01)

(52) U.S. Cl.
CPC ............ *A61B 6/5258* (2013.01); *A61B 6/032* (2013.01); *A61B 6/4441* (2013.01); *A61B 6/466* (2013.01); *A61B 6/5205* (2013.01); *A61B 6/56* (2013.01); *G06T 11/00* (2013.01); *A61B 6/4291* (2013.01)

(58) Field of Classification Search
CPC ..................................................... A61B 6/5258
See application file for complete search history.

(56) References Cited

U.S. PATENT DOCUMENTS

| 7,227,982 B2 | 6/2007 | De Man et al. | |
| 2003/0194048 A1* | 10/2003 | De Man ................ | G06T 11/006 378/4 |
| 2009/0175562 A1* | 7/2009 | Pan ........................ | A61B 6/032 382/312 |

* cited by examiner

*Primary Examiner* — Edwin Gunberg
(74) *Attorney, Agent, or Firm* — Sughrue Mion, PLLC

(57) ABSTRACT

Provided is a medical image photographing apparatus, including: an X-ray generator configured to radiate an X-ray toward an object that is located in a three-dimensional (3D) virtual grid space which includes a plurality of voxels; an X-ray detector comprising a plurality of detecting elements and configured to detect the X-ray that has propagated through the object; and an image processor configured to process projection image data corresponding to the detected X-ray based on a volume of a first region within the plurality of voxels, through which the X-ray propagates.

23 Claims, 15 Drawing Sheets

MEDICAL IMAGE PHOTOGRAPHING APPARATUS AND METHOD OF PROCESSING MEDICAL IMAGE

CROSS-REFERENCE TO RELATED APPLICATION

This application claims priority from Korean Patent Application No. 10-2014-0091320, filed on Jul. 18, 2014, in the Korean Intellectual Property Office, the disclosure of which is incorporated herein by reference in its entirety.

BACKGROUND

1. Field

One or more exemplary embodiments relate to a medical image photographing apparatus and a method of processing a medial image, and more particularly, to a medical image photographing apparatus and a method of processing a medical image, which are capable of reducing artifacts in a reconstructed computed tomography (CT) image.

2. Description of the Related Art

Medical imaging apparatuses are used to acquire images showing an internal structure of an object. The medical imaging apparatuses are non-invasive examination devices that capture and process images of details of structures, tissues, flow of fluid, etc., inside a body and provide the images to a user. A user, e.g., a medical practitioner, may use medical images output from the medical imaging apparatuses to diagnose a patient's condition and diseases.

A medical imaging apparatus acquires projection image data by transmitting X-rays through an object, and then reconstructs an image showing a cross-section of an object from the projection image data.

Several reconstruction methods are used during image reconstruction of an object and are classified into two main categories: non-iterative reconstruction and iterative reconstruction techniques.

Non-iterative reconstruction techniques can be divided into direct Fourier reconstruction and back-projection methods, and a back-projection method can be subdivided into filtered back-projection and back-projection filtering. Non-iterative reconstruction methods, other than a direct Fourier reconstruction method, may employ back-projection whereby an image acquired when X-rays propagate through an object and are projected onto an X-ray detector is back-projected into an image reconstruction space.

Iterative reconstruction techniques can be divided into algebraic reconstruction and statistical reconstruction methods. Both the algebraic and statistical reconstruction methods require iterations of a reconstruction process until a desired image is obtained. The process includes comparing an image obtained by projecting a virtual model with a measured image, and comparing an image obtained by modifying the virtual model via back-projection and reprojecting the resulting model with the measured image.

Projection/back-projection algorithms are indispensable for reconstruction of X-ray tomographic images.

In projection or back-projection, the contribution of a detector pixel or a voxel in a voxel grid to the magnitude of an X-ray signal is calculated. Techniques of the related art for calculating the contribution include pixel-driven, ray-driven, and distance-driven approaches. In the pixel-driven approach, a ratio of distances of two detector values from an intersection point between a virtual line passing through a midpoint of each voxel in a voxel grid and a surface of a detector is used as a weighting factor. In the ray-driven approach, a ratio of distances between a virtual line passing through a midpoint of a detector pixel and each of midpoints of two voxels adjacent to the virtual line is defined as a weighting factor. In the distance-driven approach, a ratio of overlapping areas between pixels and voxels projected onto a virtual plane is used as a weighting factor. The pixel-driven, ray-driven, and distance-driven approaches may cause artifacts to occur in a reconstructed image due to properties of a discrete pixel or voxel when calculating weighting factors.

Furthermore, when a C-arm is used as a medical image photographing apparatus, artifacts may be introduced when positions of a detector and an X-ray source finely vary according to a position and an angle of the C-arm.

Thus, it is necessary to reduce artifacts that may occur in a reconstructed image during projection and back-projection in order to improve the quality of the reconstructed image.

SUMMARY

One or more exemplary embodiments include a medical image photographing apparatus and a method for processing a medical image, which are capable of reducing artifacts that may occur in a reconstructed image.

Additional aspects will be set forth in part in the description which follows and, in part, will be apparent from the description, or may be learned by practice of the presented exemplary embodiments.

According to one or more exemplary embodiments, a medical image photographing apparatus includes: an X-ray generator configured to irradiate an X-ray toward an object that is located in a three-dimensional (3D) virtual grid space which includes a plurality of voxels; an X-ray detector comprising a plurality of detecting elements and configured to detect the X-ray that has propagated through the object; and an image processor configured to process projection image data corresponding to the detected X-ray based on a volume of a first region within the plurality of voxels, through which the X-ray has propagated.

The image processor may be further configured to process the projection image data by using a weight that is calculated based on at least one from among the volume of the first region, a volume of a portion of an overlap between the first region and at least one voxel, and a volume of one voxel.

The image processor may be further configured to obtain the projection image data by applying the calculated weight to voxel data.

The image processor may be further configured to obtain voxel data by applying the calculated weight to the projection image data.

The image processor may be further configured to set a slice in the 3D virtual grid space and to acquire, as the weight, a ratio of a volume of a portion of an overlap between the first region and at least one voxel in the slice to a volume of the at least one voxel in the slice.

The X-ray generator may be further configured to irradiate the X-ray in a form of a cone-beam or a fan-beam, and the image processor may be further configured to acquire, as the first region, a region of an overlap between the slice and a first polyhedron formed by connecting a point from which the X-ray generator irradiates the X-ray to each of a plurality of vertices lying on a face of one of the plurality of detecting elements, the face being directed toward the X-ray generator.

The image processor may be further configured to acquire a plurality of points at which two planes of the slice and edges of the first polyhedron meet and to obtain a second polyhedron having the plurality of points as vertices as the first region.

The plurality of detecting elements may be arranged such that each of the plurality of detecting elements is inclined at an equal angle with respect to the X-ray generator or each of the plurality of detecting elements is spaced at an equal distance from the X-ray generator.

The X-ray detector may be a planar detector, and the plurality of detecting elements may be arranged in one of a one-dimensional (1D) array and a two-dimensional (2D) array.

The apparatus may include a computed tomography (CT) apparatus.

The apparatus may include a C-arm medical image photographing apparatus.

According to one or more exemplary embodiments, a method for processing a medical image includes: irradiating, by an X-ray generator, an X-ray toward an object that is located in a three-dimensional (3D) virtual grid space which includes a plurality of voxels; detecting, by at least one from among a plurality of detecting elements, the X-ray that has propagated through the object; and processing projection image data corresponding to the detected X-ray based on a volume of a first region within the plurality of voxels, through which the X-ray has propagated.

The processing the projection image data may include acquiring a weight based on at least one from among the volume of the first region, a volume of a portion of an overlap between the first region and at least one voxel, and a volume of one voxel.

The processing the projection image data may include obtaining the projection image data by applying the acquired weight to voxel data.

The processing the projection image data may include obtaining voxel data by applying the acquired weight to the projection image data.

The weight may be determined by calculating a ratio of a volume of at least one voxel in a slice set in the 3D virtual grid space to a volume of a portion of an overlap between the first region and the at least one voxel in the slice.

The irradiating the X-ray may include irradiating the X-ray in a form of a cone-beam or a fan-beam, and the first region may be a region of an overlap between the slice and a first polyhedron formed by connecting a point of origination of the irradiating the X-ray to each of a plurality of vertices lying on a face of one of the plurality of detecting elements, the face being directed toward the X-ray generator.

The first region may be a second polyhedron having as vertices a plurality of points at which two planes of the slice and edges of the first polyhedron meet.

The plurality of detecting elements may be arranged such that each of the plurality of detecting elements is inclined at an equal angle with respect to the X-ray generator or each of the plurality of detecting elements is spaced at an equal distance from the X-ray generator.

The plurality of detecting elements may be arranged in one of a 1D array and a 2D array so as to form a planar detector.

The method may be implemented by using a CT apparatus.

The method may be implemented by using a C-arm medical image photographing apparatus.

The method may be implemented by using a Positron Emission Tomography (PET)/CT apparatus.

According to an exemplary embodiment, by calculating a weight based on a volume of a portion through which X-rays propagate during projection and back-projection, an accuracy of a calculation of the weight may be increased, compared to a method of the related art. Furthermore, even when a position between a detector and an X-ray source varies slightly due to gravity or rotation, an accuracy of a calculation of a weight may be improved.

The medical image photographing apparatus and the method for processing a medical image according to the exemplary embodiments facilitate an execution of a reconstruction of a medical image with minimized artifacts.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
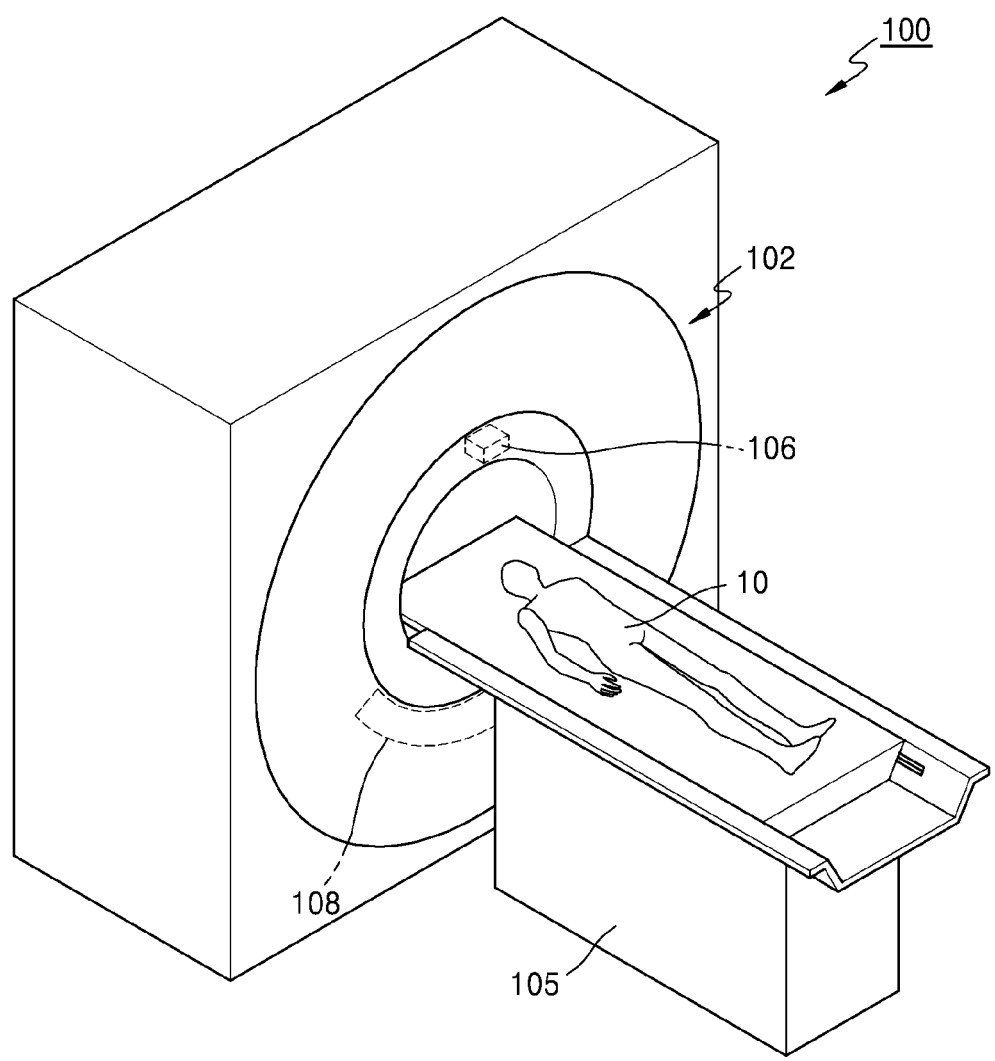
FIG. 1 is a schematic diagram of a general computed tomography (CT) system.

Advantages and features of one or more exemplary embodiments and methods of accomplishing the same may be understood more readily by reference to the following detailed description of the exemplary embodiments and the accompanying drawings. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art, and the present inventive concept will only be defined by the appended claims. Like reference numerals refer to like elements throughout the specification.

Hereinafter, the terms used in the specification will be briefly defined, and the exemplary embodiments will be described in detail.

The terms used in this specification are those general terms currently widely used in the art in consideration of functions regarding the present inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the exemplary embodiments refers to a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units". Expressions such as "at least one of," when preceding a list of elements, modify the entire list of elements and do not modify the individual elements of the list.

Reference will now be made in detail to exemplary embodiments, examples of which are illustrated in the accompanying drawings. In this regard, the present exemplary embodiments may have different forms and should not be construed as being limited to the descriptions set forth herein. In the following description, well-known functions or constructions are not described in detail so as not to obscure the exemplary embodiments with unnecessary detail.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

Throughout the specification, a "CT image" may mean an image generated by synthesizing a plurality of X-ray images that are obtained by photographing an object while a CT imaging apparatus rotates around at least one axis with respect to the object.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. The object may be a phantom. The phantom means a material having a density, an effective atomic number, and a volume that are approximately the same as those of an organism. For example, the phantom may be a spherical phantom having properties similar to the human body.

Throughout the specification, a "user" may be, but is not limited to, a medical expert including a medical doctor, a nurse, a medical laboratory technologist, a medial image expert, or a technician who repairs a medical apparatus.

Since a CT system is capable of providing a cross-sectional image of an object, the CT system may distinctively express an inner structure, e.g., an organ such as a kidney or a lung, of the object, as compared to a general X-ray imaging apparatus.

The CT system may obtain a plurality of pieces of image data with a thickness not more than 2 mm at a speed of between several tens per second to several hundred times per second, and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to enable a user to easily observe an area of interest in volume rendering.

Voxel of interest (VOI)—a method of displaying only a selected area in volume rendering.

A CT system 100 according to an exemplary embodiment will now be described with reference to FIG. 1. The CT system 100 may include any of various types of devices.

FIG. 1 schematically illustrates the CT system 100. Referring to FIG. 1, the CT system 100 may include a gantry 102, a table 105, an X-ray generating unit (also referred to herein as an "X-ray generator") 106, and an X-ray detecting unit (also referred to herein as an "X-ray detector") 108.

The gantry 102 may include the X-ray generating unit 106 and the X-ray detecting unit 108.

An object 10 may be positioned on the table 105.

The table 105 may be configured to move in a predetermined direction (e.g., at least one of up, down, right, and left directions) during a CT imaging procedure. In addition, the table 105 may be configured to tilt and/or rotate by a predetermined angle in a predetermined direction.

The gantry 102 may also be configured to tilt by a predetermined angle in a predetermined direction.

Figure 2:
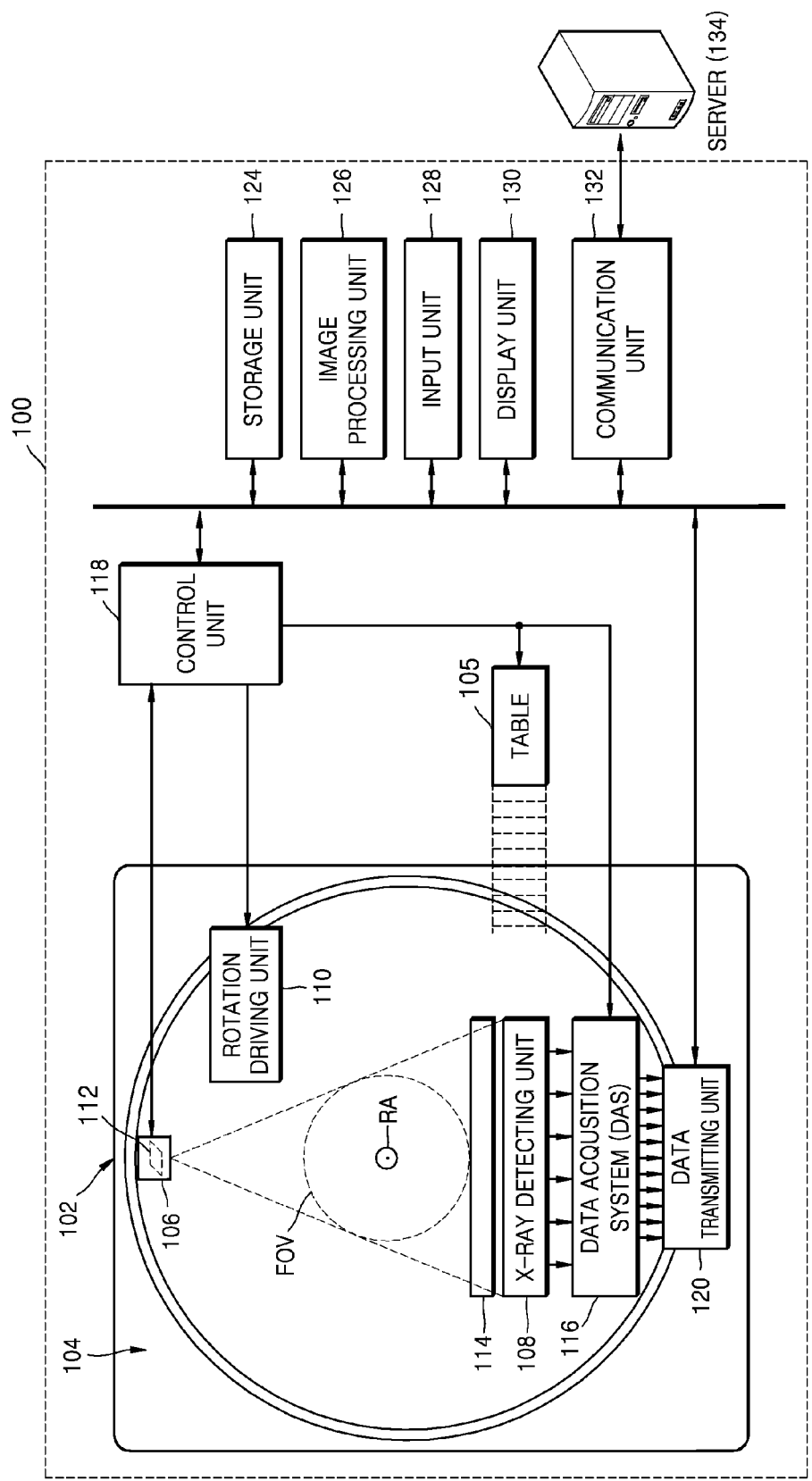
FIG. 2 is block diagram of a structure of a CT system, according to an exemplary embodiment.

FIG. 2 is a block diagram illustrating a structure of the CT system 100.

The CT system 100 may include the gantry 102, the table 105, a control unit (also referred to herein as a "controller") 118, a storage unit (also referred to herein as a "storage device" and/or as a "storage") 124, an image processing unit (also referred to herein as an "image processor") 126, an input unit (also referred to herein as an "input device") 128, a display unit (also referred to herein as a "display device" and/or as a "display") 130, and a communication unit (also referred to herein as a "communicator" and/or as a "transceiver") 132.

As described above, the object 10 may be positioned on the table 105. In the present exemplary embodiment, the table 105 may move in a predetermined direction (e.g., at least one of up, down, right, and left directions), and movement of the table 105 may be controlled by the control unit 118.

The gantry 102 may include a rotating frame 104, the X-ray generating unit 106, the X-ray detecting unit 108, a rotation driving unit (also referred to herein as a rotation driver") 110, a data acquisition system (DAS) 116, and a data transmitting unit (also referred to herein as a "data transmitter") 120.

The gantry 102 may include the rotating frame 104 having a loop shape and capable of rotating with respect to a predetermined rotation axis RA. Alternatively, the rotating frame 104 may have a disc shape.

The rotating frame 104 may include the X-ray generating unit 106 and the X-ray detecting unit 108 that are arranged to face each other so as to have predetermined fields of view FOV. The rotating frame 104 may also include an anti-scatter grid 114. The anti-scatter grid 114 may be positioned between the X-ray generating unit 106 and the X-ray detecting unit 108.

In a medical imaging system, X-ray radiation that reaches a detector (or a photosensitive film) includes not only attenuated primary radiation that forms a valuable image, but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material, such as a solid polymer material, solid polymer, or a fiber composite material. However, formation of the anti-scatter grid 114 is not limited thereto.

The rotating frame 104 may receive a driving signal from the rotation driving unit 110 and may rotate the X-ray generating unit 106 and the X-ray detecting unit 108 at a predetermined rotation speed. The rotating frame 104 may receive the driving signal and power from the rotation driving unit 110 while the rotating frame 104 contacts the rotation driving unit 110 via a slip ring (not shown). Further, the rotating frame 104 may receive the driving signal and power from the rotation driving unit 110 via wireless communication.

The X-ray generating unit 106 may receive a voltage and current from a power distribution unit (PDU) (not shown) (also referred to herein as a "power distributor") via a slip ring (not shown) and then a high voltage generating unit (not shown) (also referred to herein as a "high voltage generator"), and may generate and emit an X-ray. When the high voltage generating unit applies a predetermined voltage (hereinafter, referred to as a tube voltage) to the X-ray generating unit 106, the X-ray generating unit 106 may generate X-rays having a plurality of energy spectra that correspond to the tube voltage.

The X-ray generated by the X-ray generating unit 106 may be emitted in a predetermined form due to a collimator 112.

The X-ray detecting unit 108 may be positioned to face the X-ray generating unit 106. The X-ray detecting unit 108 may be positioned to face the X-ray generating unit 106. Each of the plurality of X-ray detecting devices may establish one channel, but one or more exemplary embodiments are not limited thereto.

The X-ray detecting unit 108 may detect the X-ray that is generated by the X-ray generating unit 106 and that has propagated through the object 10, and may generate an electrical signal corresponding to an intensity of the detected X-ray.

The X-ray detecting unit 108 may include an indirect-type X-ray detector which is configured for detecting radiation after converting the radiation into light, and a direct-type X-ray detector which is configured for detecting radiation after directly converting the radiation into electric charges. The indirect-type X-ray detector may use a scintillator. Further, the direct-type X-ray detector may use a photon counting detector. The DAS 116 may be connected to the X-ray detecting unit 108. Electrical signals generated by the X-ray detecting unit 108 may be collected by wire or wirelessly by the DAS 116. Electrical signals generated by the X-ray detecting unit 108 may be collected by wire or wirelessly by the DAS 116. In addition, the electrical signals generated by the X-ray detecting unit 108 may be provided to an analog-to-digital converter (not shown) via an amplifier (not shown).

According to a slice thickness or the number of slices, only some of a plurality of pieces of data collected by the X-ray detecting unit 108 may be provided to the image processing unit 126 via the data transmitting unit 120, or the image processing unit 126 may select only some of the plurality of pieces of data.

Such a digital signal may be provided to the image processing unit 126 via the data transmitting unit 120. The digital signal may be provided to the image processing unit 126 by wire or wirelessly.

The control unit 118 may control an operation of each of the elements in the CT system 100. For example, the control unit 118 may control operations of the table 105, the rotation driving unit 110, the collimator 112, the DAS 116, the storage unit 124, the image processing unit 126, the input unit 128, the display unit 130, the communication unit 132, and/or the like.

The image processing unit 126 may receive data acquired by the DAS 116 (e.g., pure data that is data before processing), via the data transmitting unit 120, and may perform pre-processing.

The pre-processing may include, for example, any of a process of correcting a sensitivity irregularity between channels and a process of correcting signal loss due to a rapid decrease in signal strength or due to the presence of an X-ray absorbing material, such as, for example, metal.

Data output from the image processing unit 126 may be referred to as raw data or projection data. The projection data may be stored in the storage unit 124 with imaging conditions (e.g., the tube voltage, an imaging angle, etc.) during the acquisition of data.

The projection data may include a group of data values that correspond to the intensity of the X-ray that has propagated through the object 10. For convenience of description, a group of a plurality of pieces of projection data that are simultaneously obtained from all channels at the same imaging angle is referred to as a projection data set.

The storage unit 124 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processing unit 126 may reconstruct a cross-sectional image of the object 10 by using the acquired projection data set. The cross-sectional image may be a 3D image. In particular, the image processing unit 126 may reconstruct a 3D image of the object 10 by using a cone beam reconstruction method or the like, based on the acquired projection data set.

The input unit 128 may receive an external input with respect to any of an X-ray tomography imaging condition, an image processing condition, and/or the like. For example, the X-ray tomography imaging condition may include any of tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, and/or the like. Further, the image processing condition may include any of a resolution of an image, an attenuation coefficient setting for the image, setting for an image combining ratio, and/or the like.

The input unit 128 may include a device which is configured for receiving a predetermined input from an external source. For example, the input unit 128 may include any one or more of a microphone, a keyboard, a mouse, a joystick, a touch pad, a touch pen, a voice recognition device, a gesture recognition device, and/or the like.

The display unit 130 may be configured to display an X-ray image reconstructed by the image processing unit 126.

Exchanges of data, power, or the like between the aforementioned elements may be performed by using at least one of wired communication, wireless communication, and optical communication.

The communication unit 132 may perform communication with an external device, an external medical apparatus, etc. via a server 134 and/or the like. The communication will now be described with reference to FIG. 3.

Figure 3:
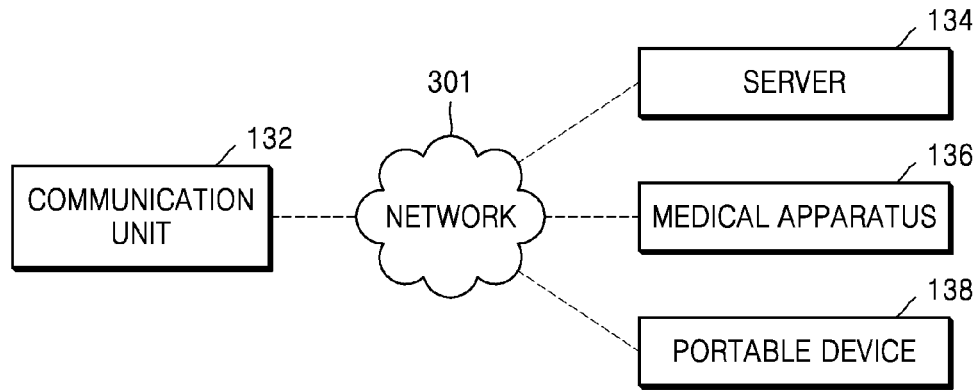
FIG. 3 is block diagram of a configuration of a communication unit.

FIG. 3 is a block diagram illustrating the communication performed by the communication unit 132.

The communication unit 132 may be wiredly or wirelessly connected to a network 301 and therefore may perform communication with the server 134, a medical apparatus 136, and/or a portable device 138. The communication module 132 may exchange data with a hospital server and/or with another medical apparatus in a hospital, which is connected thereto via a PACS.

Further, the communication unit 132 may perform data communication with portable device 138 and/or the like, according to the digital imaging and communications in medicine (DICOM) standard.

The communication unit 132 may transmit and receive data related to diagnosing the object 10 via the network 301. Further, the communication unit 132 may transmit and/or receive a medical image obtained from another medical apparatus 136 such as any of a magnetic resonance imaging (MRI) apparatus, an X-ray apparatus, and/or the like.

Furthermore, the communication unit 132 may receive a diagnosis history and/or a medical treatment schedule about a patient from the server 134 and may use the diagnosis history or the medical treatment schedule to diagnose the patient. In addition, the communication unit 132 may perform data communication not only with the server 134 or medical apparatus 136 in a hospital, but also with portable device 138 of a user or patient.

Still further, the communication unit 132 may transmit information about a device error, information about a quality control status, and/or the like to a system manager or a service manager via the network 301, and may receive a feedback regarding the information from the system manager or service manager.

Figure 4:
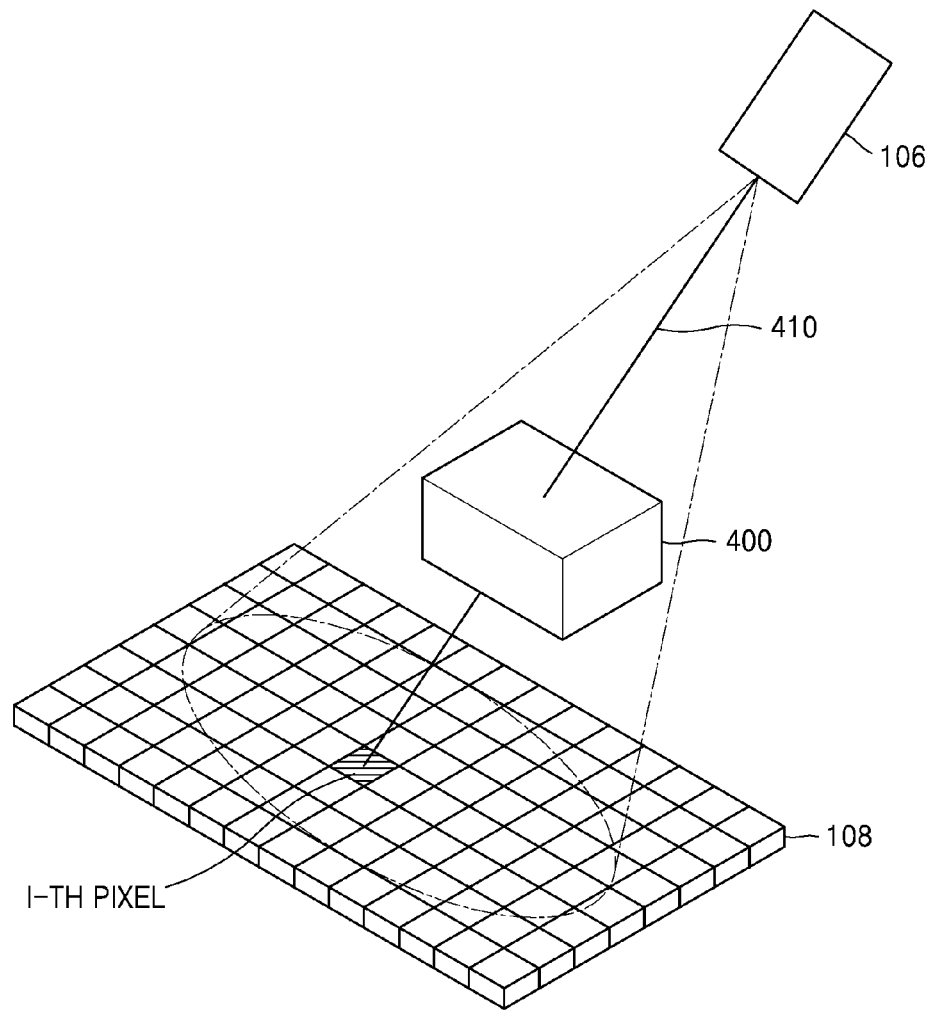
FIG. 4 is a diagram which illustrates processing of a medical image, according to an exemplary embodiment.

FIG. 4 is a diagram which illustrates processing of a medical image, according to an exemplary embodiment.

Referring to FIG. 4, an X-ray that is irradiated toward an object 400 propagates through the object 400 to an X-ray detector 108. A process of obtaining projection data by detecting an X-ray that has passed through the object 400, performed by the X-ray detector 108, will now be described in detail with reference to FIG. 4.

An X-ray generator 106 emits an X-ray toward the object 400. The emitted X-ray may be in a form of a cone-beam or a fan-beam, but is not limited thereto. The X-ray then passes through the object 400 to the X-ray detector 108, which is segmented into individual pixels as shown in FIG. 4. The object 400 is located on a path between the X-ray detector 108 and the X-ray generator 106, along which the X-ray is irradiated, and the X-ray is attenuated as it passes through the object 400. Thus, by measuring the amount of X-ray reaching a pixel in the X-ray detector 108, the degree to which the X-ray is attenuated when passing through the object 400 may be detected, and information about the inside of the object 400 may be obtained.

Figure 5:
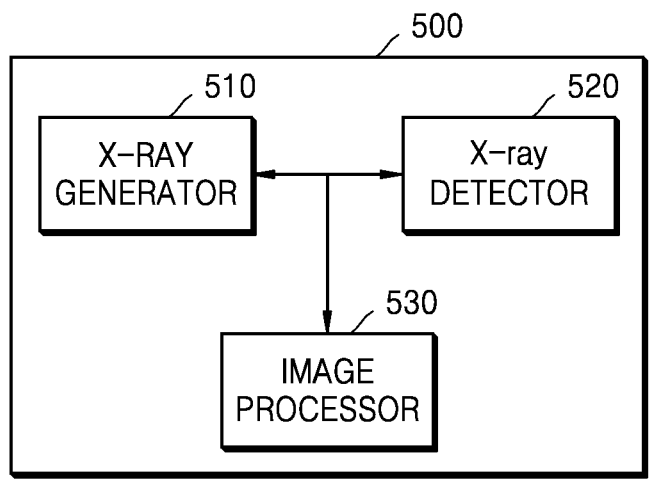
FIG. 5 illustrates a configuration of a medical image photographing apparatus, according to an exemplary embodiment.

FIG. 5 illustrates a configuration of a medical image photographing apparatus 500, according to an exemplary embodiment.

Referring to FIG. 5, the medical image photographing apparatus 500 according to the present exemplary embodiment includes an X-ray generator 510, an X-ray detector 520, and an image processor 530.

The X-ray generator 510 emits an X-ray onto an object located in a 3D virtual grid space composed of a plurality of voxels. The X-ray detector 520 detects an X-ray reaching a plurality of detecting elements (pixels). The image processor 530 processes projection image data corresponding to the X-ray detected by the X-ray detector 520, based on a volume of a region within the plurality of voxels, through which the X-ray passes.

A medical image photographing apparatus according to an exemplary embodiment may be a CT apparatus for reconstructing a CT image by performing CT scanning, and may be incorporated into or connected to the CT system 100 described with reference to FIGS. 1, 2, and 3 for its operation.

In detail, when the medical image photographing apparatus 500 is incorporated into the CT system 100, the X-ray generator 510, the X-ray detector 520, and the image processor 530 included in the medical image photographing apparatus 500 may be the X-ray generating unit 106, the X-ray detecting unit 108, and the image processing unit 126 in the CT system 100, respectively. Alternatively, the medical image photographing apparatus 500 may be included in the medical apparatus 136 or portable device 138 shown in FIG. 3 and configured to receive a detection signal corresponding to a detected X-ray from the CT system 100 for its operation. Furthermore, the image processor 530 of the medical image photographing apparatus 500 may be included in the medical apparatus 136 or the portable device 138, and the X-ray generator 510 and the X-ray detector 520 may be included in the CT system 100.

The medical image photographing apparatus 500 may also be a medical imaging apparatus for reconstructing a 3D CT image by using a volume rendering (VR) technique.

Figure 6:
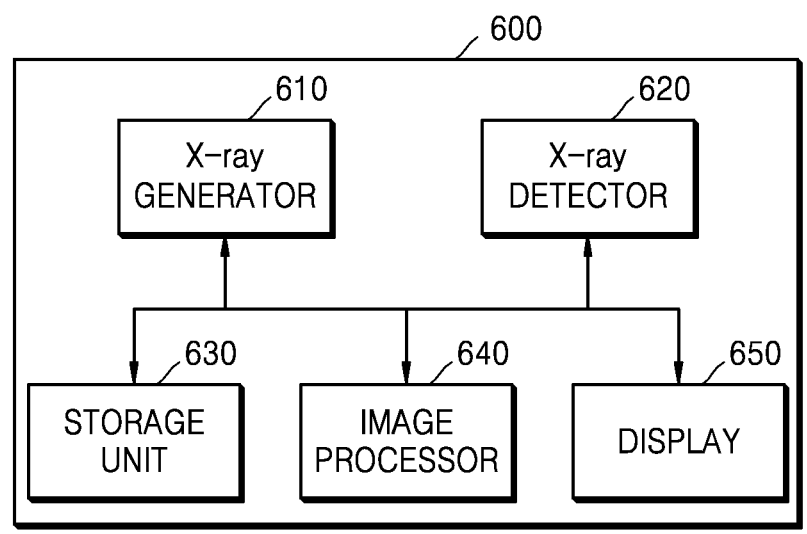
FIG. 6 illustrates a configuration of a medical image photographing apparatus, according to another exemplary embodiment.

FIG. 6 illustrates a configuration of a medical image photographing apparatus 600 according to another exemplary embodiment. Referring to FIG. 6, the image photographing apparatus 600 according to the present exemplary embodiment includes an X-ray generator 610, an X-ray detector 620, a storage unit 630, an image processor 640, and a display 650.

As described above with reference to FIG. 5, the medical image photographing apparatus 600 may be incorporated into or connected to the CT system 100 described with reference to FIGS. 1, 2, and 3 for its operation.

In detail, when the medical image photographing apparatus 600 is incorporated into the CT system 100, the X-ray generator 610, the X-ray detector 620, the storage unit 630, the image processor 640, and the display 650 may respectively correspond to the X-ray generating unit 106, the X-ray detecting unit 108, the storage unit 124, the image processing unit 126, and the display unit 130 in the CT system 100.

Alternatively, the medical image photographing apparatus 600 may be included in the medical apparatus 136 or portable device 138 shown in FIG. 3 and configured to receive a detection signal corresponding to a detected X-ray from the CT system 100 for its operation. Furthermore, the storage unit 630, the image processor 640, and the display 650 of the medical image photographing apparatus 600 may be included in the medical apparatus 136 or the portable device 138, and the X-ray generator 610 and the X-ray detector 620 may be included in the CT system 100 of FIG. 1.

Similarly, the medical image photographing apparatus 600 may also be a medical imaging apparatus for reconstructing a 3D CT image by using a volume rendering (VR) technique.

It is assumed hereinafter that the medical image photographing apparatus 600 generates a CT image and reconstructs a 3D CT image by using a VR technique.

Figure 7:
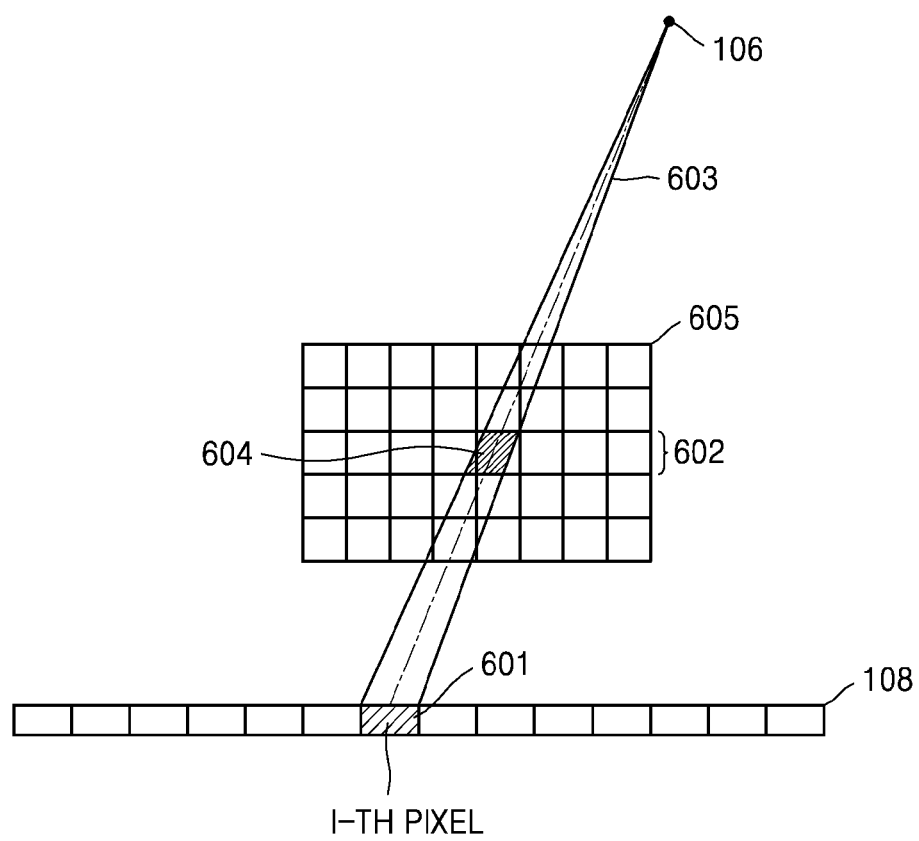
FIG. 7 is another diagram which illustrates processing of a medical image, according to an exemplary embodiment.

FIG. 7 is another diagram which illustrates processing of a medical image, according to an exemplary embodiment.

In detail, FIG. 7 illustrates a cross-section when FIG. 4 is viewed from a side. An object (not shown) is located in a 3D virtual grid space 605 composed of a plurality of voxels. The object may be a part of a body that is undergoing CT scanning.

Referring to FIG. 7, the 3D grid space 605 may have a quadrangular shape when viewed from a side. If a 3D object (not shown) is located in the 3D grid space 605, a cross-section of the 3D object may also be represented as a cross-section of a quadrangular voxel having a uniform size. Different parts of the object corresponding to different voxels may be formed of different materials.

FIG. 7 shows a path 603 of an X-ray that is emitted by an X-ray generator 106 and that propagates through the object (not shown) to an i-th pixel 601 of an X-ray detector 108, and a region 604 where the X-ray passes through a k-th slice 602 is located in the path 603 of the X-ray.

Figure 8:
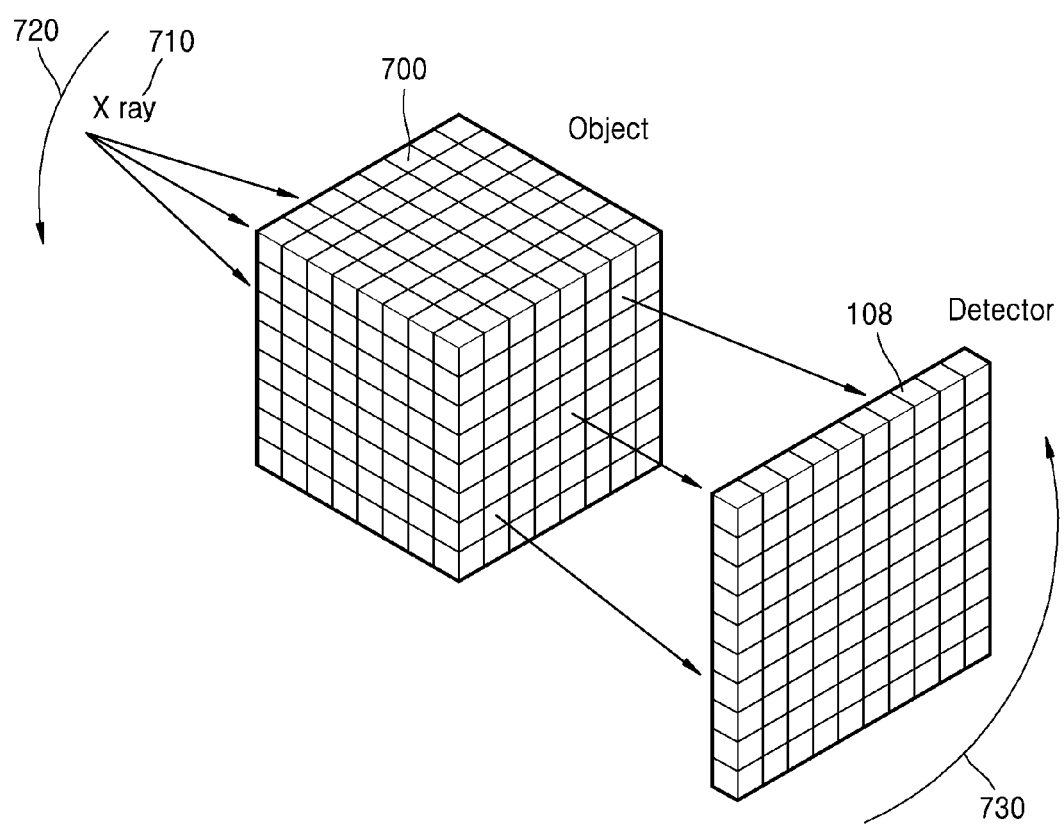
FIG. 8 is a diagram which illustrates processing of projection image data obtained when an X-ray passes through an object.

FIG. 8 is a diagram which illustrates processing of projection image data obtained when an X-ray propagates through an object. For convenience of explanation, cross-sections of hexahedral voxels are represented on a cross-section of a hexahedral object 700.

When the X-ray detector 108 detects an X-ray that has passed through the object 700, projection image data may be obtained. An X-ray radiator (not shown) may rotate in a direction indicated by an arrow 720 in FIG. 8 while the X-ray detector 108 is rotating in a direction indicated by an arrow 730 at the same time.

When P is a matrix that represents a data value (pixel value) on each detecting element (pixel) of a detector, A is a matrix that represents weights of voxels in a 3D grid space through which an X-ray incident on a detecting element has propagated, and X is a matrix that represents a density value or attenuation coefficient for each voxel in the 3D grid space, the matrix P is calculated by applying weights to the matrix X, as shown in Equation (1). Furthermore, as defined by Equation (2), the matrix X may be obtained by calculating the matrix A by converting all values at different projection angles into vectors and then solving a linear algebraic equation by using the inverse of the matrix A.

$$AX=P \tag{1}$$

$$A^{-1}AX=A^{-1}P=X \tag{2}$$

Although a density value or attenuation coefficient of the object 700 may be calculated by using an inverse matrix, calculating matrices A for all projection angles and all detecting elements (pixels) and inverses thereof requires an enormous amount of data and is extremely difficult to implement. Thus, a projection/back-projection algorithm may be used to calculate only values necessary for reconstructing a tomographic image.

Figure 9A:
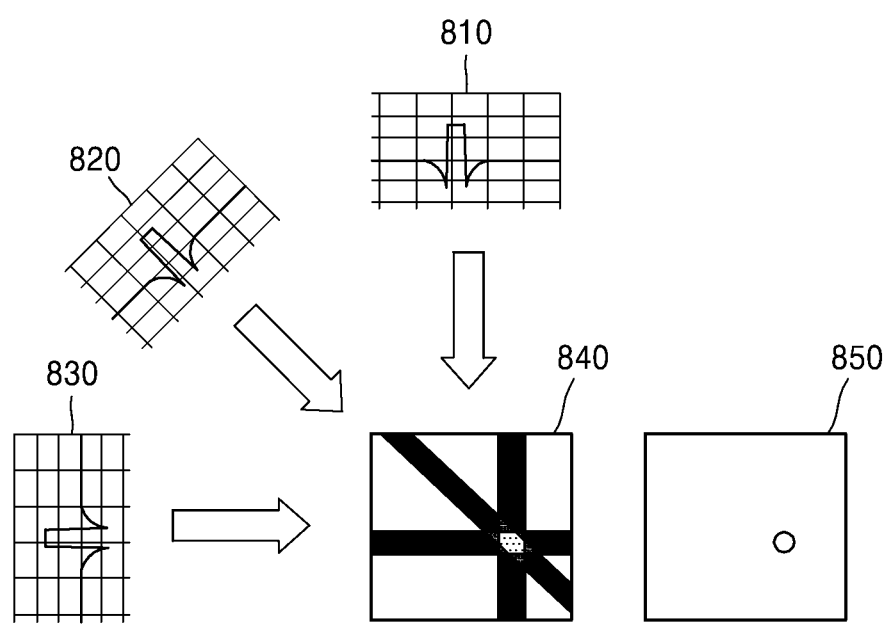
FIG. 9A is a diagram which illustrates capturing of a medical image and reconstruction of an image.

FIG. 9A is a diagram which illustrates photographing of a medical image and reconstruction of a tomographic image.

Methods of reconstructing a tomographic image may be primarily classified into non-iterative and iterative reconstruction techniques.

A back-projection method, which is one type of the non-iterative reconstruction techniques, can be divided into two approaches: filtered back-projection and back-projection filtering. The two approaches use back-projection to reconstruct projection data acquired by an X-ray detector into a 3D space.

According to the back-projection method, an image is reconstructed by adding up projection data acquired from a plurality of directions back across an image plane. The back-projection method facilitates an acquisition of an image that is similar to the real image by using projection data acquired from a plurality of directions.

In detail, FIG. 9A shows that a medical image photographing apparatus (not shown) captures a medical image as the medical image photographing apparatus rotates around an object (not shown), and acquires data that corresponds to a captured medical image. For example, in a CT apparatus, an X-ray generator (not shown) may generate an X-ray and irradiate the X-ray toward an object, and an X-ray detector (not shown) may detect the X-ray that has passed through the object and produce data that corresponds to the detected X-ray.

A plurality of filtered projection data obtained by filtering a plurality of projection data acquired from a plurality of X-ray irradiation directions, e.g., a plurality of filtered projection data 810, 820, and 830, are projected back and added to obtain an image 840. Alternatively, an image 850 may be obtained by adding up more projection data than just the three projection data 810, 820, and 830.

Figure 9B:
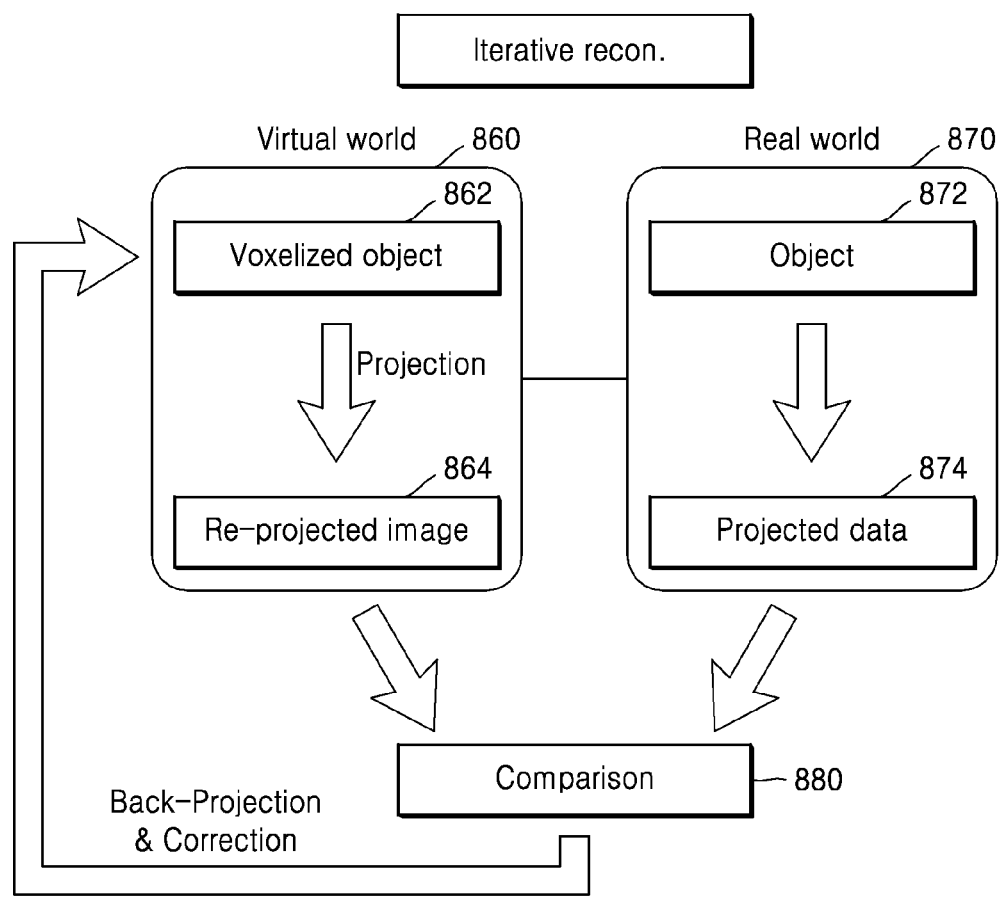
FIG. 9B is a flowchart of a method for reconstructing an image using an iterative reconstruction technique.

FIG. 9B is a flowchart of a method for reconstructing an image by using an iterative reconstruction technique.

Iterative reconstruction techniques may be primarily divided into algebraic reconstruction methods and statistical reconstruction methods. Both the algebraic and statistical reconstruction methods include comparing a re-projected image (or data) 864 obtained by projecting a voxelized object 862 on a virtual world 860 with projected data (or a projection image) 874 obtained by transmitting an X-ray which propagates through an object 872 onto a real world 870 (i.e., operation 880) and modifying a virtual model via back-projection (i.e., operation 890). Thereafter, an operation of comparing projection data (or a projection image) obtained by projecting the modified virtual model with the projection data (or projection image) obtained by transmitting the X-ray through a real model (the object 872) is iteratively performed until a desired image is obtained. For example, if a difference between the re-projected image 864 and the projected data 874 falls within an error range set by a user, an iterative reconstruction process stops, and a final image may be obtained.

Figure 10A:
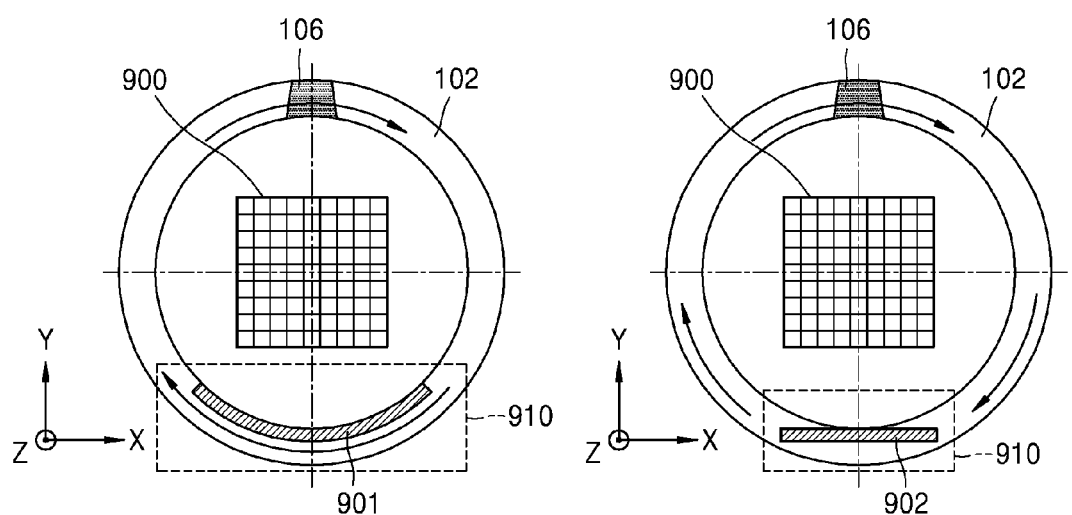
FIG. 10A illustrates an example of a medical image photographing apparatus, according to an exemplary embodiment.
Figure 10B:
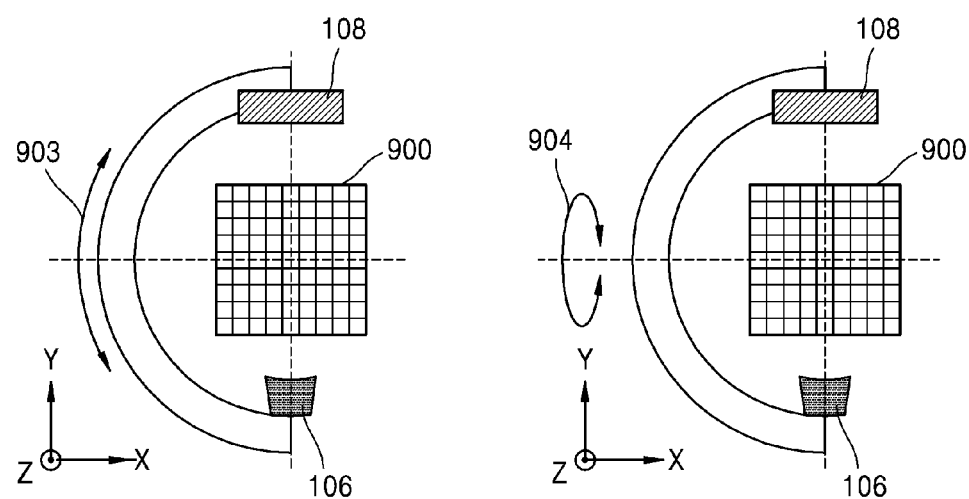
FIG. 10B illustrates another example of a medical image photographing apparatus, according to another exemplary embodiment.

FIGS. 10A and 10B illustrate medical image photographing apparatuses according to exemplary embodiments.

Referring to FIG. 10A, a medical image photographing apparatus according to an exemplary embodiment may be a CT apparatus. Referring to FIG. 10B, a medical image photographing apparatus according to another exemplary embodiment may be a C-arm type apparatus. For example, the C-arm type apparatus may be a C-arm Positron Emission Tomography (PET)/CT apparatus. However, the present exemplary embodiment is merely an example, and therefore, exemplary embodiments are not limited thereto.

The medical image photographing apparatus of FIG. 10A, i.e., the CT apparatus, may include an X-ray generator 106, an X-ray detector 910, and an image processor (126 of FIG. 2). As shown in FIG. 10A, the X-ray detector 910 may be a curved detector 901 which includes a plurality of detecting elements that are all inclined at an equal angle to or spaced at an equal distance from the X-ray generator 106. Alternatively, the X-ray detector 910 may be a planar detector 902 which includes a plurality of detecting elements that are arranged in a one-dimensional (1D) or 2D array, but exemplary embodiments are not limited thereto.

The X-ray detector 910 may detect an X-ray that is emitted by the X-ray generator 106 and that has propagated through a voxelized object 900. The image processor 126 may process projection image data which corresponds to the X-ray detected by the X-ray detector 910 based on a volume of a region within the plurality of voxels through which the X-ray has propagated. As described below with reference to FIG. 13, the plurality of detecting elements in the X-ray detector 910 may have a quadrangular shape but are not limited thereto.

Referring to FIG. 10B, the medical image photographing apparatus, i.e., the C-arm type apparatus, may include an X-ray generator 106, an X-ray detector 108, and an image processor (126 of FIG. 2). The X-ray detector 108 may detect an X-ray that is emitted by the X-ray generator 106 and that has propagated through a voxelized object 900. As described above with reference to FIG. 10A, a plurality of detecting elements in the X-ray detector 108 may have a quadrangular shape but are not limited thereto.

The C-arm type apparatus may rotate about a Y axis or an X axis in a direction indicated by an arrow 903 or 904, respectively, but the direction of rotation is not limited thereto. The image processor 126 may process projection image data which corresponds to the X-ray detected by the X-ray detector 108 based on a volume of a region within the plurality of voxels through which the X-ray has propagated.

Figure 11:
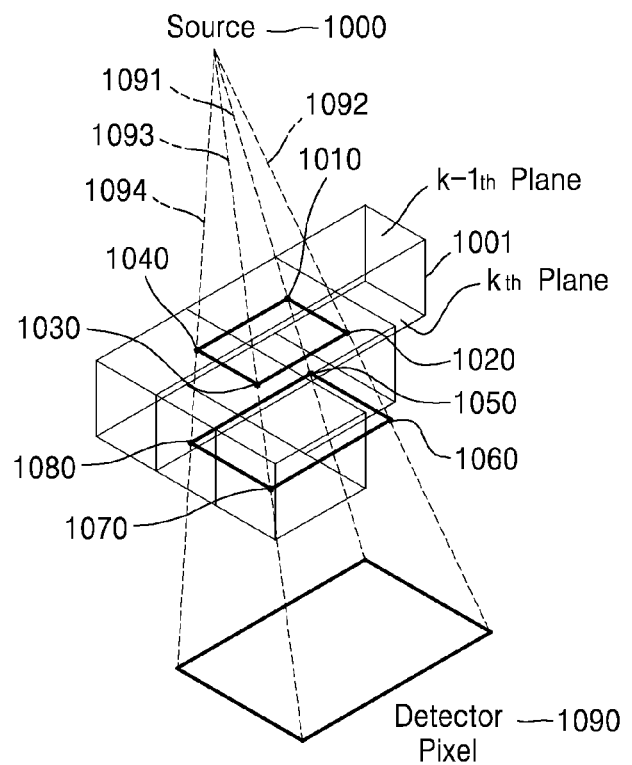
FIG. 11 is a diagram which illustrates processing of projection image data, according to an exemplary embodiment.

FIG. 11 is a diagram which illustrates processing of projection image data, according to an exemplary embodiment. In detail, FIG. 11 illustrates a method for processing a projected image by using projection data generated by transmitting an X-ray through the object (400 of FIG. 4).

FIG. 11 shows a slice 1001 in a 3D grid space which includes a plurality of voxels and which further includes k−1-th and k-th planes. If an X-ray emitted by an X-ray radiator (not shown) has passed through the slice 1001, a pixel 1090 that is a detecting element in an X-ray detector (not shown) may detect the X-ray that has passed through the slice 1001. Furthermore, a volume of a region in the slice 1001 through which the X-ray has passed may be computed by calculating a path along which the X-ray has passed through the slice 1001 to the pixel 1090. A weight may be calculated by computing the volume of the region, and a medical image may be processed based on the calculated weight. A method of computing a volume of a region through which an X-ray has passed will now be described in more detail.

Referring to FIG. 11, a polyhedron may be generated that includes lines 1091, 1092, 1093, and 1094 and sides contained in the pixel 1090 as edges. The lines 1091 through 1094) respectively connect a point from which the X-ray generator irradiates the X-ray (i.e., a point of origination of the irradiation of the X-ray) to each of four vertices that lie on a face of the pixel 1090 directed toward the X-ray generator.

As shown in FIG. 11, the polyhedron may be a quadrangular pyramid, but is not limited thereto. The shape of the polyhedron may vary according to a shape of the pixel 1090. For convenience, the polyhedron is hereinafter referred to as a 'first region'.

A region of an overlap between the first region and the slice 1001 is hereinafter referred to as an overlap region. As shown in FIG. 11, the overlap region may be a hexahedron which includes, as vertices, points 1010, 1020, 1030, and 1040 contained in the k−1-th plane and points 1050, 1060, 1070, and 1080 contained in the k-th plane. Similarly, the overlap region is not limited to a hexahedron, and may have different shapes according to a shape of the pixel 1090.

The points 1010, 1020, 1030, and 1040 may be points of intersections between the lines 1091 through 1094 and the k−1-th plane, respectively.

Similarly, the points 1050, 1060, 1070, and 1080 may be points of intersections between the lines 1091 through 1094 and the k-th plane, respectively.

The image processor (126 of FIG. 2) may calculate a weight based on at least one of a volume of the overlap region, a volume of a portion of an overlap between the overlap region and one or more voxels, and a volume of one voxel, and may process projection image data based on the calculated weight. As described below with reference to FIG. 12C, the overlap region may be a tilted hexahedron 1210, and the 'volume of a portion of overlap between the overlap region and one or more voxels' may be a volume of a region 1220 indicated by oblique lines.

A weight may be calculated for each pixel, and if a weight for each pixel is represented by the matrix A as described with reference to FIG. 8, voxel data or pixel data may be obtained using Equation (1) or (2) as shown above.

In this aspect, if a weight is applied to voxel data using Equation (1), projection image data (pixel data) may be obtained. If a weight is applied to the projection image data (pixel data) using Equation (2), voxel data may be obtained.

A method of processing projection image data will now be described in more detail with reference to FIGS. 12A, 12B, and 12C.

Figure 12A:
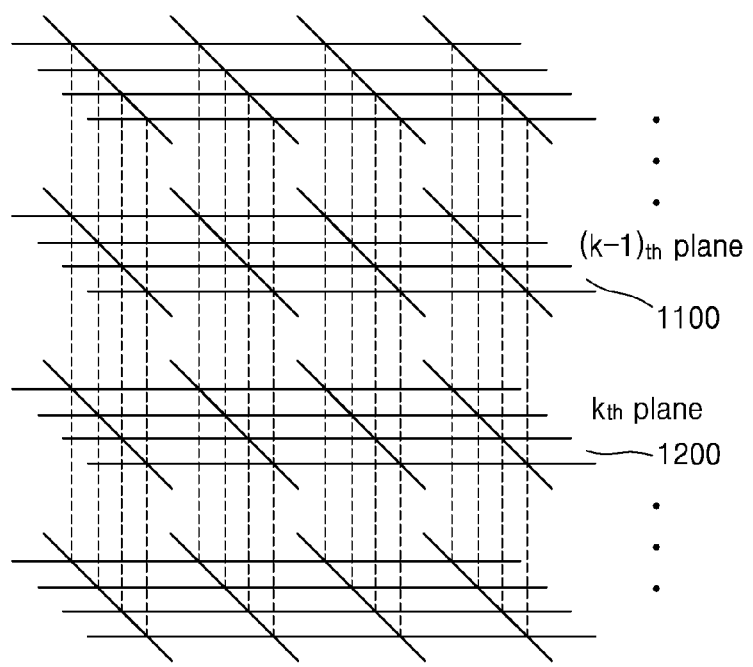
FIG. 12A illustrates slices in a three-dimensional (3D) grid space, according to an exemplary embodiment.

FIG. 12A illustrates slices in a 3D grid space, according to an exemplary embodiment. A slice 1001 may be formed by k−1-th and k-th planes 1100 and 1200 from among a plurality of planes in a 3D virtual grid space.

Figure 12B:
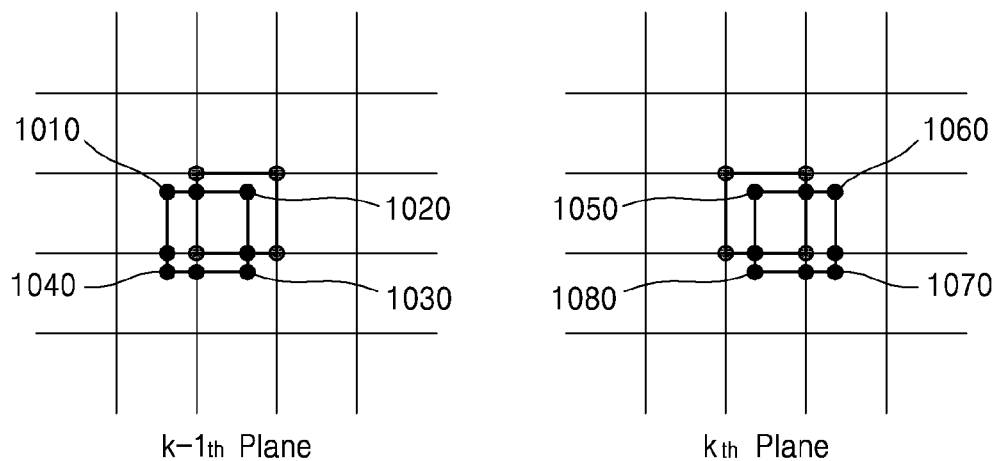
FIG. 12B illustrates cross-sections of slices in a 3D grid space, according to an exemplary embodiment.

FIG. 12B illustrates cross-sections of slices in a 3D grid space, according to an exemplary embodiment.

In detail, FIG. 12B shows points 1010, 1020, 1030, and 1040 contained in the k−1-th plane of the slice 1001 shown in FIG. 11 and points 1050, 1060, 1070, and 1080 contained in the k-th plane.

Figure 12C:
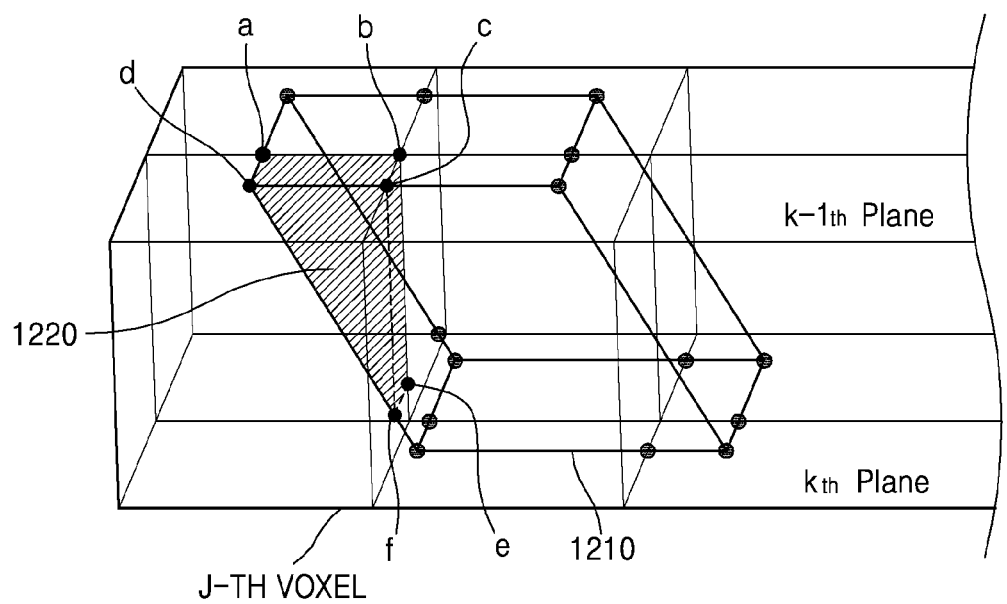
FIG. 12C illustrates a region in a slice in a 3D grid space through which an X-ray passes, according to an exemplary embodiment.

FIG. 12C illustrates a region in a slice in a 3D grid space through which an X-ray has propagated, according to an exemplary embodiment.

Referring to FIG. 12C, a volume of a portion of an overlap between a j-th voxel and the overlap region having, as vertices, the points 1010, 1020, 1030, and 1040 contained in the k−1-th plane and the points 1050, 1060, 1070, and 1080 contained in the k-th plane may be indicated by oblique lines.

In detail, the volume of the portion of overlap between the overlap region and the j-th voxel may be a volume of a polyhedron having points a, b, c, d, e, and f as vertices. Similarly, a volume of a portion of an overlap between the overlap region and another one of the remaining voxels in the slice may be calculated.

Although FIG. 12C shows that the volume of the portion of overlap between the overlap region and the j-th voxel is calculated, exemplary embodiments are not limited thereto. For example, a weight may be calculated by using a volume of a portion of an overlap between the overlap region and two or more voxels.

Calculating the volume of the portion of the overlap may include dividing the portion into a plurality of tetrahedrons, calculating a volume of each of the tetrahedrons and adding up volumes of the tetrahedrons A portion of overlap with one voxel (hereinafter, referred to as the 'overlap portion') may form a polyhedron that is divided into a plurality of tetrahedrons. If one of the plurality of tetrahedrons has vertices with coordinates a, b, c, and d, a volume of the tetrahedron may be calculated by using Equation (3) below:

$$V = \frac{|(\vec{a}-\vec{d}) \cdot ((\vec{b}-\vec{d}) \times (\vec{c}-\vec{d}))|}{6} \quad (3)$$

where $\vec{a}$, $\vec{b}$, $\vec{c}$, and $\vec{d}$ are vectors respectively corresponding to the coordinates a, b, c, and d of the four vertices.

In addition, the volume of the overlap portion may be calculated by finding an area of faces enclosing the overlap portion and using the area. When $S_j$ (j=0, 1, . . . , n) corresponds to polygonal faces of the overlap portion, $Q_j$ is an arbitrary point on the polygonal face Sj, Nj is a unit normal vector that points outward from the polygonal face $S_j$, and $P_{0j}$, $P_{1j}$, . . . , $P_{mj}$ are vertices lying on the polygonal faces $S_j$, the volume of the overlap portion is expressible by Equation (5) by using an area of a polygonal surface $S_j$ calculated by Equation (4) below:

$$\text{Area}(S_j) = \frac{1}{2}\left|N_j \cdot \left\{\sum_k P_{kj} \times P_{k+1,j}\right\}\right| \quad (4)$$

$$\text{Volume(Polyhedron)} = \frac{1}{3}\left|\sum_j (Q_j \cdot N_j)\text{Area}(S_j)\right| \quad (5)$$

In this case, if $Q_j = P_{0j}$, $$N_j = \{(P_{1j}-P_{0j}) \times (P_{1j}-P_{0j})\}/|(P_{1j}-P_{0j}) \times (P_{2j}-P_{0j})|$$

and the volume of the overlap portion that is a polyhedron may be expressible by Equation (6):

$$\text{Volume(Polyhedron)} = \frac{1}{6}\left|\left[\sum_j (P_{0j} \cdot N_j)\left|N_j \cdot \left\{\sum_k P_{kj} \times P_{k+1,j}\right\}\right|\right]\right| \quad (6)$$

Similarly, a volume of a portion of overlap between the overlap region and at least one voxel may also be calculated by using Equations (4), (5), and (6).

Figure 13A:
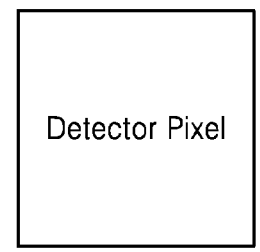
FIG. 13A illustrates a shape of a detecting element of an X-ray detector, according to an exemplary embodiment.
Figure 13B:
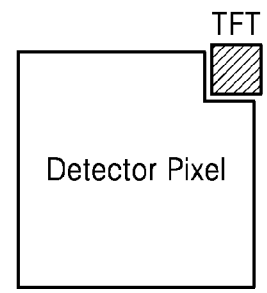
FIG. 13B illustrates another shape of a detecting element of an X-ray detector, according to an exemplary embodiment.
Figure 13C:
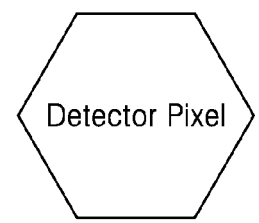
FIG. 13C illustrates another shape of a detecting element of an X-ray detector, according to an exemplary embodiment.

FIGS. 13A, 13B, and 13C illustrate shapes of the X-ray detector 108, 901 or 902, according to an exemplary embodiment.

In detail, referring to FIG. 13A, a detecting element (pixel) of the X-ray detector 108, 901, or 902 has a quadrangular shape. Referring to FIG. 13B, a detecting element of the X-ray detector 108, 901, or 902 has a quadrangular shape including a thin film transistor (TFT). Referring to FIG. 13C, a detecting element has a hexahedral shape. Exemplary embodiments are not limited thereto, and a detecting element may have various other shapes.

Figure 14:
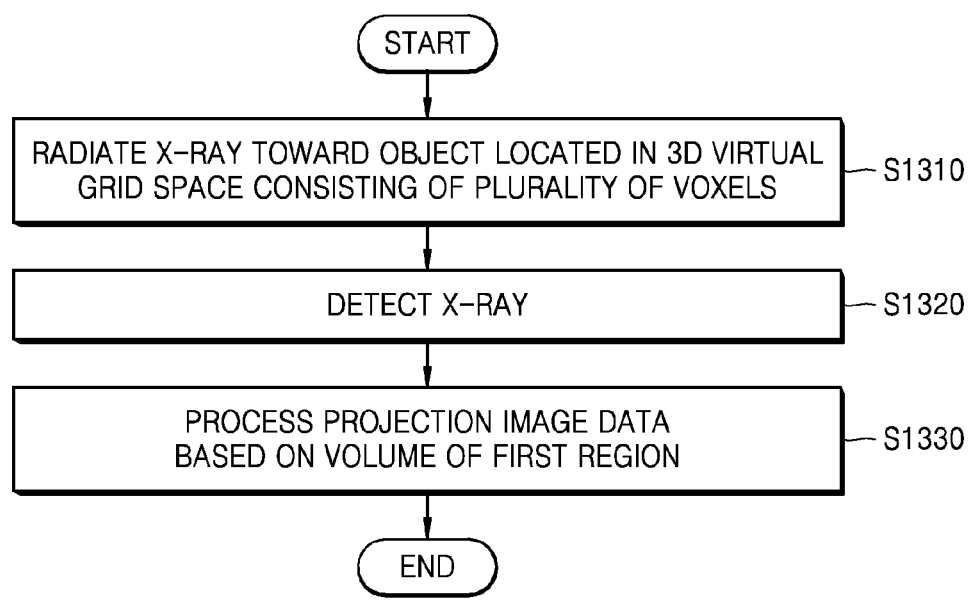
FIG. 14 is a flowchart of a method for processing a medical image, according to an exemplary embodiment.

FIG. 14 is a flowchart of a method for processing a medical image, according to an exemplary embodiment.

Since the method according to the present exemplary embodiment may include the same operations as those of the medical image photographing apparatus 500 of FIG. 5, the same descriptions as already presented with respect to FIGS. 1 through 13 are omitted.

Referring to FIGS. 5 and 14, in operation S1310, an X-ray is irradiated toward an object located in a 3D virtual grid space which includes a plurality of voxels. Operation S1310 may be performed by the X-ray generator 510 of the medical image photographing apparatus 500.

In operation S1320, the X-ray that is irradiated toward and that has propagated through the object is detected. Operation S1320 may be performed by the X-ray detector 520.

In operation S1330, projection image data corresponding to the detected X-ray is processed based on a volume of a first region within the plurality of voxels, through which the X-ray has propagated. Operation S1330 may be performed by the image processor 530.

Furthermore, operation S1330 may include obtaining a weight based on at least one of the volume of the first region, a volume of a portion of an overlap between the first region and one or more voxels, and a volume of one voxel.

In addition, operation S1330 may include acquiring projection image data by applying a weight to voxel data and/or obtaining voxel data by applying a weight to projection image data.

Figure 15:
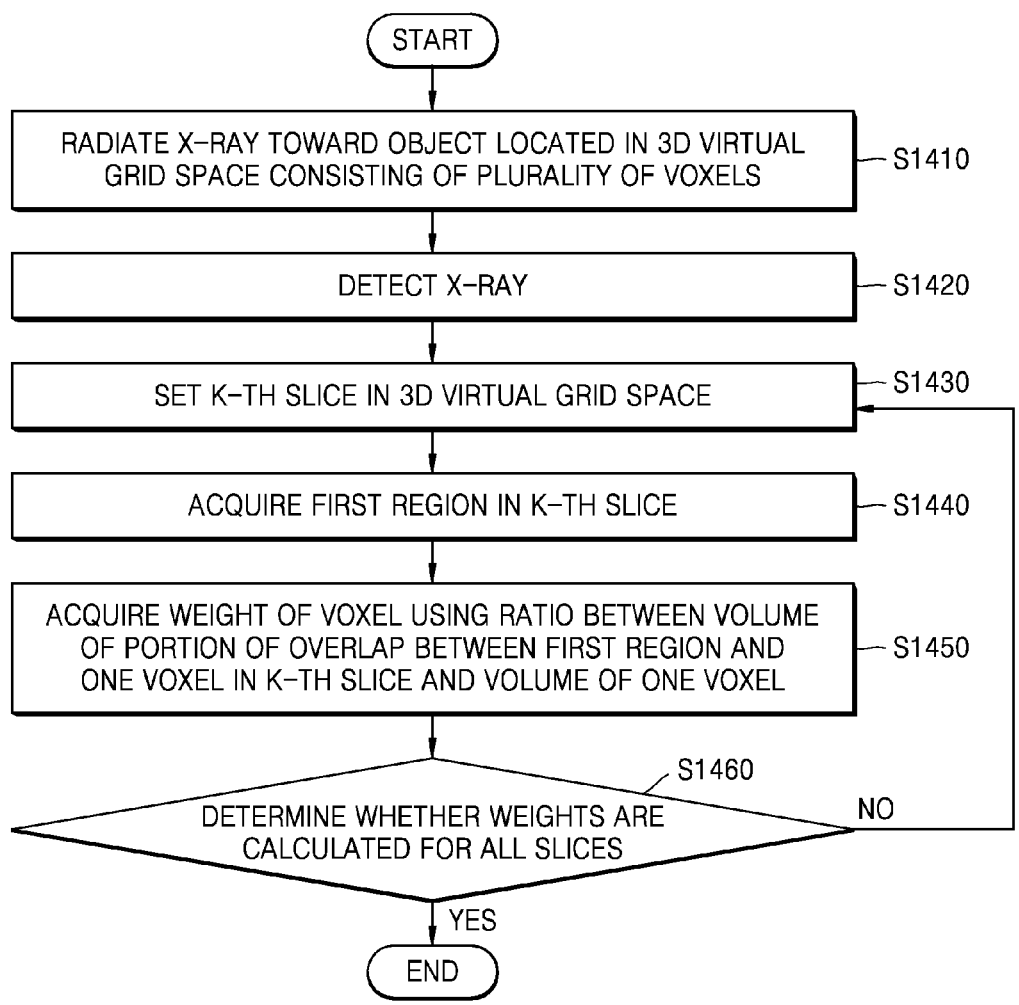
FIG. 15 is a flowchart of a method for processing a medical image, according to another exemplary embodiment.

FIG. 15 is a flowchart of a method for processing a medical image, according to another exemplary embodiment. Since the method according to the present exemplary embodiment may include the same operations as those of the medical image photographing apparatus (500 of FIG. 5), the same descriptions as already presented with respect to FIGS. 1 through 13 are omitted.

Referring to FIGS. 5 and 15, in operation S1410, an X-ray is irradiated toward an object located in a 3D virtual grid space which includes a plurality of voxels. Operation S1410 may be performed by the X-ray generator 510 of the medical image photographing apparatus 500.

In operation S1420, the X-ray that is irradiated toward and that has propagated through the object is detected. Operation S1420 may be performed by the X-ray detector 520.

In operation S1430, a k-th slice is set in the 3D virtual grid space where the X-ray is irradiated.

In operation S1440, a first region in the k-th slice is obtained.

The first region may be a region of an overlap between the k-th slice and a first polyhedron that is formed by respectively connecting a point from which the X-ray generator 510 irradiates the X-ray to each of a plurality of vertices lying on a face of one of a plurality detecting elements of the X-ray detector 520, which is directed toward the X-ray generator 510.

Alternatively, the first region may be a second polyhedron having, as vertices, a plurality of points at which two planes of the k-th slice and edges of the first polyhedron meet.

In operation S1450, a weight of a voxel is calculated by using a ratio of a volume of a portion of an overlap between the first region and one voxel in the k-th slice to a volume of the voxel. Operations S1430, S1440, and S1450 may be performed by the image processor 530.

In operation S1460, a determination is made as to whether respective weights have been calculated for all slices. If weights are not calculated for all slices in operation S1450, the process returns to operation S1430, and another slice is set in the 3D virtual grid space. If weights are calculated for all slices, the process is terminated.

The plurality of detecting elements of the X-ray detector 520 may be all inclined at an equal angle to or spaced at an equal distance from the X-ray generator 510. Furthermore, the plurality of detecting elements of the X-ray detector 108 may have the same area and be arranged in a 1D array or a 2D array to form a planar detector. However, exemplary embodiments are not limited thereto.

The methods of FIGS. 14 and 15 may be performed by a CT apparatus. Furthermore, the methods may also be used in a C-arm type apparatus. The C-arm type apparatus may be a PET/CT apparatus, but is not limited thereto.

Figure 16:
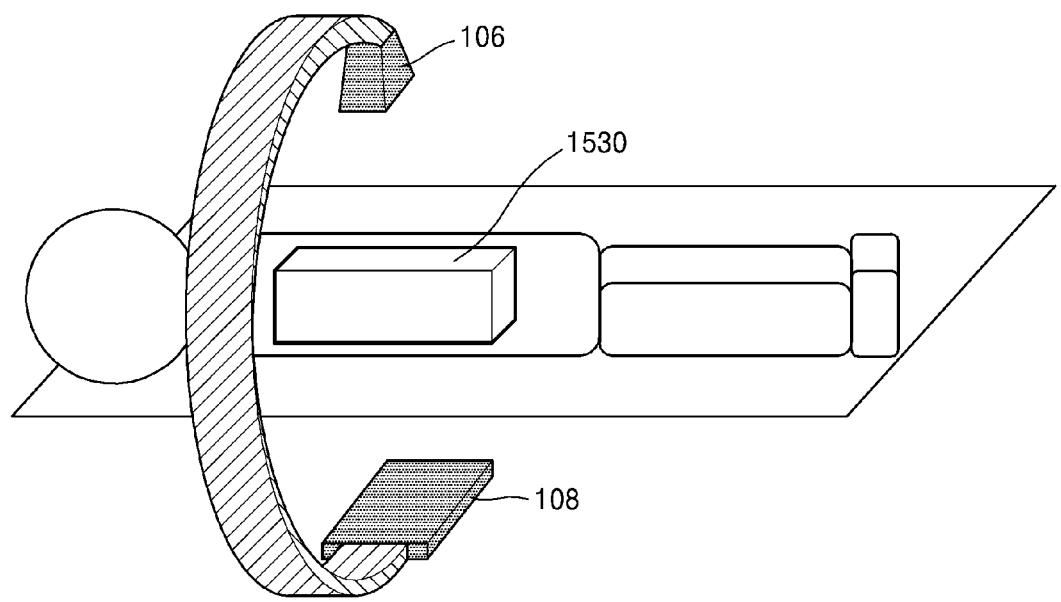
FIG. 16 illustrates a medical image photographing apparatus, according to another exemplary embodiment.

FIG. 16 illustrates a medical image photographing apparatus, according to another exemplary embodiment. Referring to FIG. 16, the medical image photographing apparatus according to the present exemplary embodiment is a C-arm type apparatus for processing a medical image. As described above with reference to FIG. 10B, the medical image photographing apparatus may include an X-ray generator 106, an X-ray detector 108, and an image processor (not shown). The X-ray detector 108 may detect an X-ray that is irradiated toward and has propagated through an object 1530.

The exemplary embodiments may be written as computer programs and may be implemented in general-use digital computers that execute the programs using a non-transitory computer-readable recording medium.

Examples of the non-transitory computer-readable recording medium include magnetic storage media (e.g., ROM, floppy disks, hard disks, etc.), optical recording media (e.g., CD-ROMs, or DVDs), etc.

While one or more exemplary embodiments have been described with reference to the figures, it will be understood by those of ordinary skill in the art that various changes in form and details may be made therein without departing from the spirit and scope as defined by the following claims. Accordingly, the above exemplary embodiments and all aspects thereof are examples only and are not limiting.

What is claimed is:

1. A medical image photographing apparatus comprising:
an X-ray generator configured to irradiate an X-ray toward an object that is located in a three-dimensional (3D) virtual grid space which includes a plurality of voxels;
an X-ray detector comprising a plurality of detecting elements and configured to detect the X-ray that has propagated through the object; and
an image processor configured to process projection image data corresponding to the detected X-ray based on a volume of a predefined first region within the plurality of voxels, through which the X-ray has propagated,
wherein the medical image photographing apparatus further comprises one from among a computed tomography (CT) apparatus, a C-arm medical image photographing apparatus, and a Positron Emission Tomography (PET)/CT apparatus, and
wherein the X-ray generator is further configured to irradiate the X-ray in a form of a cone-beam or a fan-beam, and
wherein the image processor is further configured to set a slice in the 3D virtual grid space and to acquire, as the first region, a region of an overlap between the slice and a first polyhedron formed by connecting a point from which the X-ray generator irradiates the X-ray to each of a plurality of vertices lying on a face of one of the plurality of detecting elements, the face being directed toward the X-ray generator.

2. The apparatus of claim 1, wherein the image processor is further configured to process the projection image data by using a weight that is calculated based on at least one from among the volume of the first region, a volume of a portion of an overlap between the first region and at least one voxel, and a volume of one voxel.

3. The apparatus of claim 2, wherein the image processor is further configured to obtain the projection image data by applying the calculated weight to voxel data.

4. The apparatus of claim 2, wherein the image processor is further configured to obtain voxel data by applying the calculated weight to the projection image data.

5. The apparatus of claim 2, wherein the image processor is further configured to acquire, as the weight, a ratio of a volume of a portion of an overlap between the first region and at least one voxel in the slice to a volume of the at least one voxel in the slice.

6. The apparatus of claim 1, wherein the image processor is further configured to acquire a plurality of points at which two planes of the slice and edges of the first polyhedron meet and to obtain a second polyhedron having the plurality of points as vertices as the first region.

7. The apparatus of claim 1, wherein the plurality of detecting elements is arranged such that each of the plurality of detecting elements is inclined at an equal angle with respect to the X-ray generator or each of the plurality of detecting elements is spaced at an equal distance from the X-ray generator.

8. The apparatus of claim 1, wherein the X-ray detector is a planar detector, and the plurality of detecting elements is arranged in one of a one-dimensional (1D) array and a two-dimensional (2D) array.

9. The apparatus of claim 1, further comprising a computed tomography (CT) apparatus.

10. The apparatus of claim 1, further comprising a C-arm medical image photographing apparatus.

11. The apparatus of claim 1, further comprising a Positron Emission Tomography (PET)/CT apparatus.

12. A method for processing a medical image, the method comprising:
    irradiating, by an X-ray generator of a medical image photographing apparatus, an X-ray toward an object that is located in a three-dimensional (3D) virtual grid space which includes a plurality of voxels;
    detecting, by at least one from among a plurality of detecting elements of the medical image photographing apparatus, the X-ray that has propagated through the object; and
    processing projection image data corresponding to the detected X-ray based on a volume of a predefined first region within the plurality of voxels, through which the X-ray has propagated,
    wherein the medical image photographing apparatus further comprises one from among a computed tomography (CT) apparatus, a C-arm medical image photographing apparatus, and a Positron Emission Tomography (PET)/CT apparatus, and
    wherein the irradiating the X-ray comprises irradiating the X-ray in a form of a cone-beam or a fan-beam, and
    wherein the first region is a region of an overlap between a slice set in the 3D virtual grid space and a first polyhedron formed by connecting a point of origination of the irradiating the X-ray to each of a plurality of vertices lying on a face of one of the plurality of detecting elements, the face being directed toward the X-ray generator.

13. The method of claim 12, wherein the processing the projection image data comprises acquiring a weight based on at least one from among the volume of the first region, a volume of a portion of an overlap between the first region and at least one voxel, and a volume of one voxel.

14. The method of claim 13, wherein the processing the projection image data comprises obtaining the projection image data by applying the acquired weight to voxel data.

15. The method of claim 13, wherein the processing the projection image data comprises obtaining voxel data by applying the acquired weight to the projection image data.

16. The method of claim 13, wherein the weight is determined by calculating a ratio of a volume of at least one voxel in the slice set in the 3D virtual grid space to a volume of a portion of an overlap between the first region and the at least one voxel in the slice.

17. The method of claim 12, wherein the first region is a second polyhedron having as vertices a plurality of points at which two planes of the slice and edges of the first polyhedron meet.

18. The method of claim 12, wherein the plurality of detecting elements is arranged such that each of the plurality of detecting elements is inclined at an equal angle with respect to the X-ray generator or each of the plurality of detecting elements is spaced at an equal distance from the X-ray generator.

19. The method of claim 12, wherein the plurality of detecting elements is arranged in at least one from among a one-dimensional (1D) array and a two-dimensional (2D) array so as to form a planar detector.

20. The method of claim 12, wherein the method is implemented by using a computed tomography (CT) apparatus.

21. The method of claim 12, wherein the method is implemented by using a C-arm medical image photographing apparatus.

22. The method of claim 12, wherein the method is implemented by using a Positron Emission Tomography (PET)/CT apparatus.

23. A non-transitory computer-readable recording medium having recorded thereon a program for executing the method of claim 12.

* * * * *